United States Patent [19]

Tovey

[11] Patent Number: 4,493,822

[45] Date of Patent: Jan. 15, 1985

[54] DOSAGE UNITS

[75] Inventor: Geoffrey D. Tovey, Harpenden, England

[73] Assignee: Smith Kline & French Laboratories Limited, Welwyn Garden City, England

[21] Appl. No.: 465,394

[22] Filed: Feb. 10, 1983

Related U.S. Application Data

[62] Division of Ser. No. 270,181, Jun. 3, 1981, Pat. No. 4,376,111.

[30] Foreign Application Priority Data

Dec. 4, 1980 [GB] United Kingdom ............... 997904
Dec. 5, 1980 [GB] United Kingdom ............. 8038993
Apr. 28, 1981 [GB] United Kingdom ............. 8112987

[51] Int. Cl.$^3$ .................... A61K 9/00; A61K 9/44; A61K 47/00
[52] U.S. Cl. .................................................. 424/15
[58] Field of Search ........................................ 424/15

[56] References Cited

U.S. PATENT DOCUMENTS

| | | |
|---|---|---|
| 60,248 | 1/1922 | Lane . |
| 91,644 | 3/1934 | Blackstone . |
| 2,386,416 | 10/1945 | Wilhelm . |
| 2,580,414 | 1/1952 | Duffey . |
| 3,532,633 | 10/1970 | Withers ................................. 252/90 |
| 4,055,178 | 10/1977 | Harrigan . |
| 4,376,111 | 3/1983 | Tovey ................................... 424/15 |

FOREIGN PATENT DOCUMENTS 690545 9/1930 France .

*Primary Examiner*—Shep K. Rose
*Attorney, Agent, or Firm*—Joseph A. Marlino; Stuart R. Suter; Alan D. Lourie

[57] ABSTRACT

The present invention provides an orally administrable pharmaceutical dosage unit having a shape such that in its most stable position on a horizontal flat surface is tilted position.

The advantage of these units is that they are more easily picked up.

The units can be made by forming the active ingredient and any excipient into the shape as defined.

10 Claims, 79 Drawing Figures

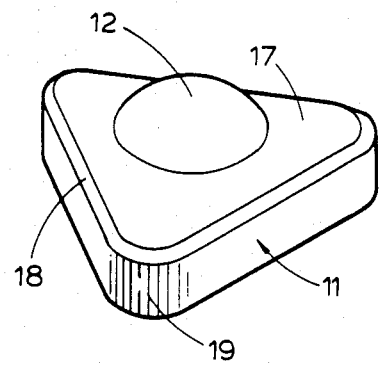
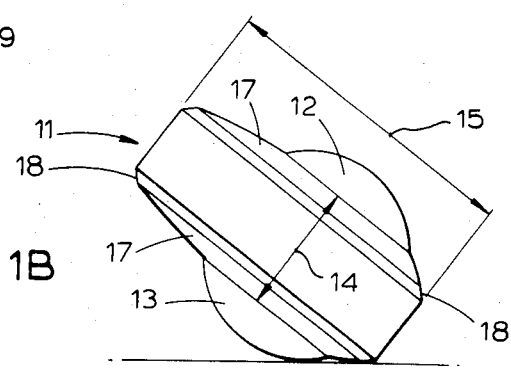
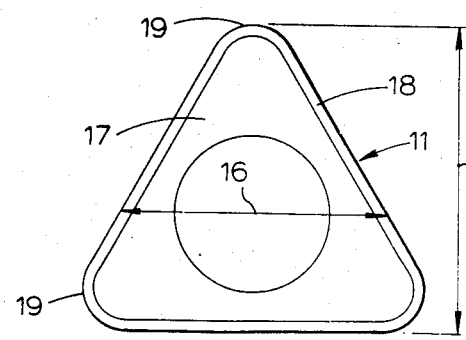

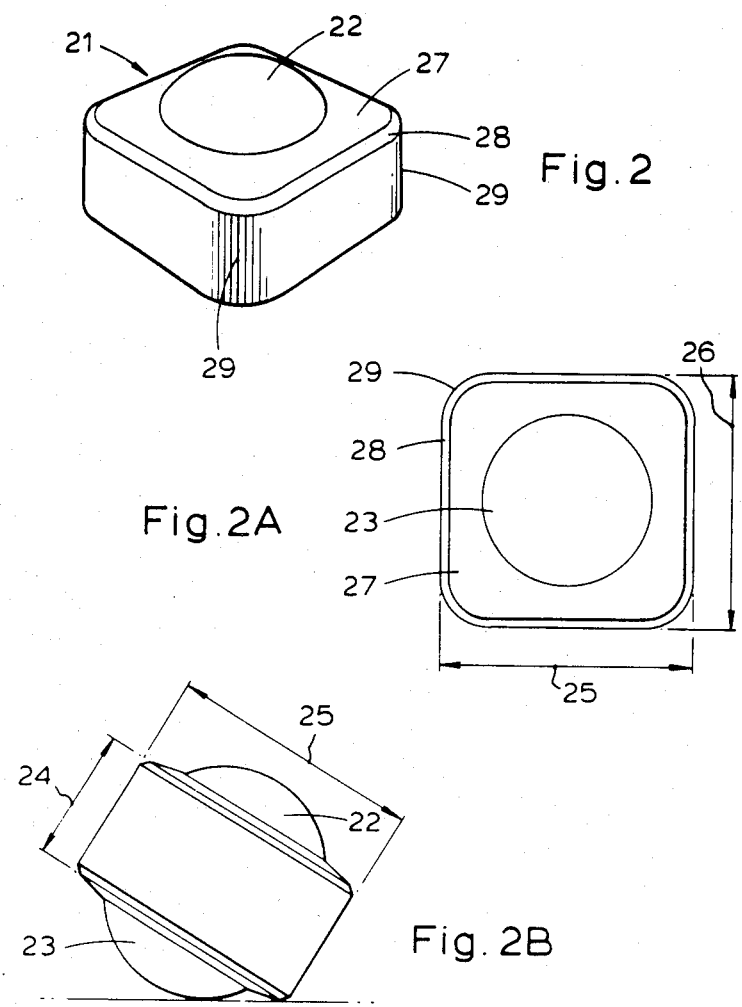

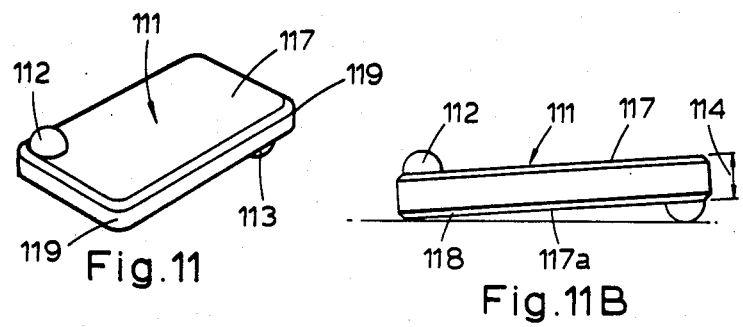
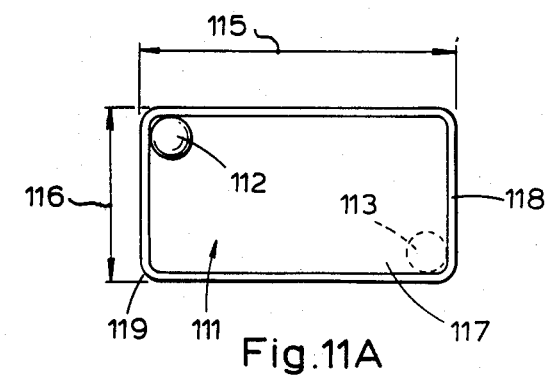
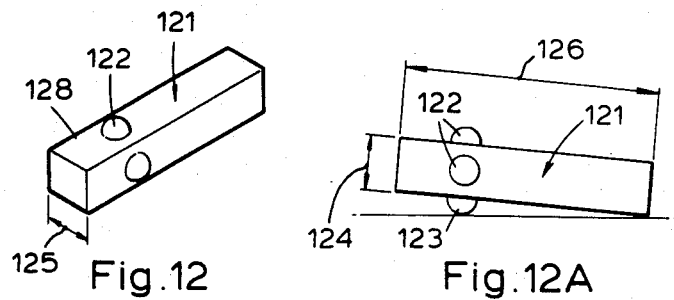

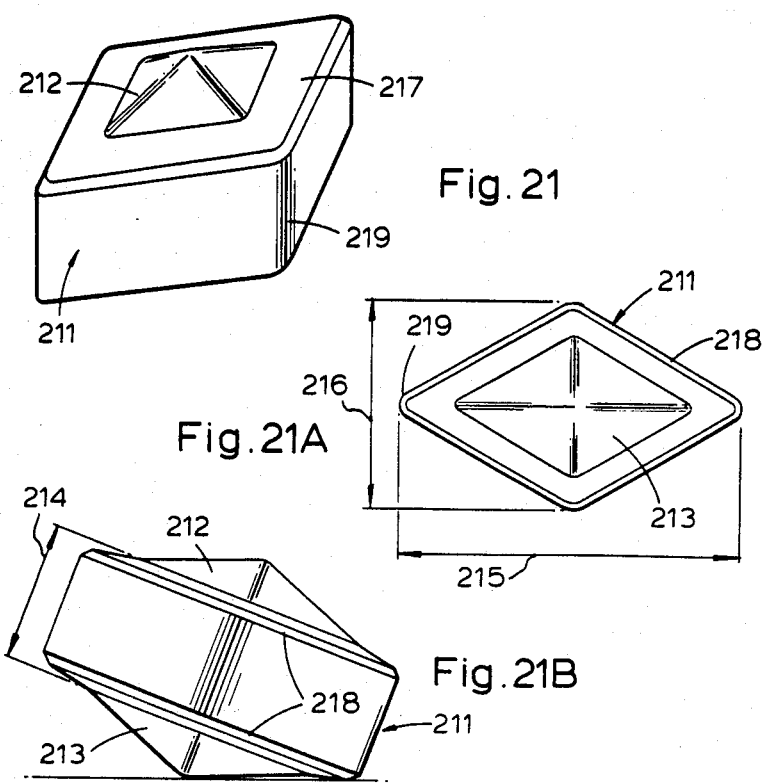
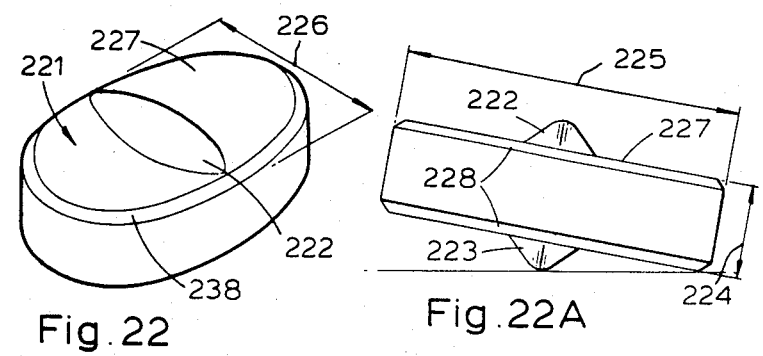

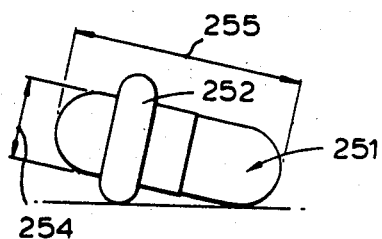 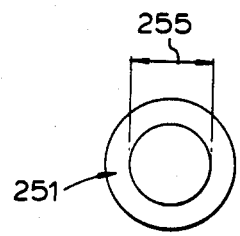
Fig. 25  Fig. 25A
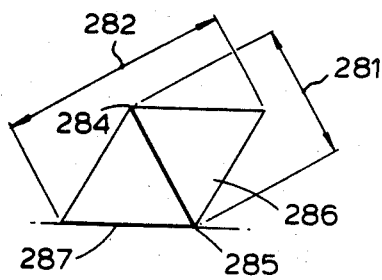 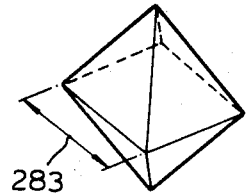
Fig. 28  Fig. 28A

DOSAGE UNITS

This is a division of application Ser. No. 270,181 filed June 3, 1981, now U.S. Pat. No. 4,376,111.

The figures in this application are related to the following U.S. design applications and corresponding patents as follows:

| Design Applications (all filed June 3, 1981) | Corresponding U.S. Design Patents (all issued July 12, 1983) |
| --- | --- |
| Serial No. 270,192 (FIG. 1) | 269,719 |
| Serial No. 270,158 (FIG. 2) | 269,715 |
| Serial No. 270,156 (FIG. 3) | 269,713 |
| Serial No. 270,157 (FIG. 4) | 269,714 |
| Serial No. 270,190 (FIG. 5) | 269,717 |
| Serial No. 270,189 (FIG. 6) | 269,716 |
| Serial No. 270,033 (FIG. 7) | 269,711 |
| Serial No. 270,191 (FIG. 8) | 269,718 |
| Serial No. 270,193 (FIG. 21) | 269,720 |
| Serial No. 270,194 (FIG. 22) | 269,721 |
| Serial No. 270,196 (FIG. 29) | 269,723 |
| Serial No. 270,195 (FIG. 30) | 269,722 |
| Serial No. 270,057 (FIG. 31) | 269,712 |

This invention relates to orally-administrable pharmaceutical dosage units and to a process for producing them.

Many medicaments are formulated as orally-administrable pharmaceutical dosage units, examples of which are tablets, capsules and lozenges. With increasing age and with certain diseases, for example, rheumatism and arthritis, patients lose manual dexterity and find it difficult to manipulate such conventional dosage units. In extreme cases this results in patients failing to comply with a prescribed course of treatment.

The concept of this invention is to gain an effective increase in height of an orally administrable dosage unit by giving it a shape such that it tilts upwards from the horizontal. The advantage of these dosage units is that they can be picked up more easily.

According to the present invention there is provided an orally-administrable pharmaceutical dosage unit which has a shape such that its most stable position on a horizontal flat surface is a tilted position.

"Most stable position" herein means the position where the centre of gravity of the unit is at its lowest point above the flat surface. Where the dosage unit is so shaped that there is more than one position where the centre of gravity is at its lowest point above the surface, all such positions are to be considered as most stable positions.

For the dosage unit to tilt it has a portion on its surface which is capable of acting as a fulcrum. In the tilted position the centre of the gravity is to one side of the fulcrum.

Pharmaceutical dosage units are three dimensional solid objects and therefore extend along three mutually perpendicular axes which are referred to herein as the vertical, longitudinal and lateral axes. The axes are assigned as follows: the shortest dimension (that is the shortest extent across the unit through the centre of gravity) lies on the vertical axis and the longest dimension (that is the longest extent across the unit through the centre of gravity in a direction normal to the vertical axis) lies on the longitudinal axis; the lateral axis is normal to the vertical and longitudinal axes. The dosage unit is in a tilted position when the plane which contains the lateral and longitudinal axes is inclined relative to the horizontal surface. Whether a dosage unit is tilted can be determined by inspection.

Where from the symmetry of the unit it is plain which is the vertical, longitudinal and lateral axes then they are assigned accordingly.

Where it is not possible to allocate the axes from the symmetry of the article then the shortest dimension is assigned as the shortest distance across the unit through the centre of gravity and the longest dimension is the longest extent across the unit through the centre of gravity in a direction normal to the shortest dimension. The lateral dimension is normal to the shortest and longest dimensions.

Where the unit has two equal shortest dimensions or where all three dimensions are equal then any one of these dimensions can be the shortest dimension.

Tilting relative to the surface can occur on the lateral or longitudinal axis or can have a component on both these axes. Where there is a component on both axes, the angle of tilt is the angle of the largest component.

The angle of tilt relative to the surface is suitably at least 5°. For example it can be at least 6°, 8° or 10°. In practice it is less than 45°. Preferably it is between 12° and 40°. In particular it is 15°, 20° or 30°.

Where the dosage unit is wholly convex, a fulcrum can be provided by the intersection of two or more surfaces meeting at an internal oblique angle. Two surfaces meeting at an internal oblique angle meet in a line, three or more surfaces meet in a point. The word convex is used here in the Euclidean sense, meaning that every straight line sector having its two end points within the shape lies entirely within the shape.

Shapes which function for the purpose of tilting as being wholly convex are to be regarded as wholly convex. Thus minor variations, for example indentations, holes, channels, and grooves which do not effect this function are regarded as not destroying convexity.

Examples of wholly convex shapes where a fulcrum is provided by the intersection of two or more surfaces are a square bipyramid, an oblate cylinder having square-pyramidal end faces, and a trigonal prism having trigonal-pyramidal end faces.

For a square bipyramid it is plain from the symmetry of the unit that one axis joins the apexes and the other two axes join the mid-points of each pair of opposite sides at the common base of both pyramids.

For an oblate cylinder having square-pyramidal end faces, one axis joins the apexes of the pyramids, a second axis is the major axis of the elliptical cross section of the cylinder and the third axis is the minor axis of the elliptical cross-section.

For a trigonal prism having trigonal-pyramidal end faces one axis joins the apexes of the pyramids, a second axis is the perpendicular height from the base of the trigonal prism to its apex and the other axis is mutually perpendicular to these two axes.

Alternatively the unit can have a main body and fulcra provided by one or more projections.

The main body, that is the basic shape of the dosage units exclusive of the projections, has three axes (herein called main body axes) and the three dimensions (herein called main body dimensions) which are assigned in relation to the main body in the same way as defined above for assigning axes and dimensions the dosage unit. For these units tilting is recognised by reference to the lateral and longitudinal main body axes.

The basic shape can be any basic shape common in the art for a pharmaceutical dosage unit.

Examples of such basic shapes where all the main body dimensions can be the same are a cube and a right cylinder having a diameter length.

The basic shape can also be one having a longest main body dimension and two shorter main body dimensions. Preferably the ratio of the longest dimension to these shortest dimensions is from 2.5:1 to 3.5:1. One example of such a shape is an elongate parallelipiped.

Preferably the two shorter main body dimensions are equal. An example of a shape in which they are is an elongate right cylinder where the shorter main body dimensions are two perpendicular diameters. A more typical and preferable shape is that referred to in the art as the capsule-shape, which consists of a cylindrical body having two convex (usually domed or frustoconical) ends. Suitably a capsule is 17.5 mm long by 6 mm in diameter.

The basic shape can also be one having two substantially equal longest main body dimensions and one short main body dimension. Examples of such shapes are a squat right parallelipiped and the conventional circular tablet shape, that is, a right cylinder, where the longest main body dimensions are two perpendicular diameters and the shortest main body dimension is the height.

When the basic shape has two substantially equal longest main body dimensions, preferably the ratio of the shortest to the longest of these dimensions is in the range 1:2 to 1:3.5. When the basic shape of the dosage unit has such dimensions, preferably it is that of a conventional circular tablet (for which suitable dimensions are 10 mm in diameter by 4 mm high or 17 mm in diameter by 6.5 mm) or a right parallelipiped (for which suitable dimensions are 7.5 mm by 7.5 mm wide by 3 mm).

Preferably the main body has two faces one at each end of the shortest dimension (forming the top and bottom faces of the unit) and a number of side faces. In particular it can have from three to eight side faces and especially three, four or five side faces for example three as in a trigonal prism.

Units of this basic shape are preferable because they roll less readily.

Preferably any edges or corners on the basic shape of the dosage unit are chamfered or rounded. For example where the basic shape is a cube, the edges of all six faces can be chamfered; where the basic shape is that a regular trigonal prism, the edges of the triangular faces can be chamfered and the corners joining the triangular faces can be rounded; where the basic shape is a squat right parallelipiped, the corners joining these largest faces can be rounded and the edges of the two largest faces can be chamfered; and where the basic shape is a squat cylinder, the edges of the circular faces can be chamfered.

It will of course be appreciated that minor variations in shape for example indentations, holes, channels and grooves are regarded as not effecting the basic shape.

The shape, size, number and position of the projections are selected relative to the basic shape and size of the dosage unit such that when the unit is placed on a flat horizontal surface in its most stable position, the unit is resting on at least one projection and the plane containing the lateral and longitudinal main body axes is tilted relative to the surface.

The projection can be for example a stud or a ridge. Preferably the projection is a stud.

Where the projection is a stud it can be cubic, right parallelipedal, pyramidal or a dome-shaped. Where the stud is pyramidal, it can be a trigonal, square, or pentagonal pyramid. Any edges or points on the projections are preferably chamfered or rounded.

When the stud is dome-shaped it can have one or more facets on its surface. For example it can have one, two, three or four facets.

Preferably when the stud is dome-shaped it is rounded.

When the projection is a ridge it can have a triangular, rectangular or curved cross-section throughout.

The size of the projection can be determined empirically, depending upon the angle of tilt required for any particular unit.

A simple cube can adopt six equivalent most stable positions on a flat surface, that is to say when it is resting on the surface on one of its faces. Accordingly where the basic shape of the dosage unit is a cube, one projection is required on each face. Thus each face can have a projection in the form of a stud or a ridge.

A right cylinder of diameter length has three most stable positions, that is to say, when it is resting on one of its two flat faces or its curved side. Such a dosage unit requires one projection on each end face and at least three studs so disposed around the circumference to ensure tilting or, a functional equivalent, for example a circumferencial ridge.

An elongate cylinder and specifically a capsule-shaped dosage unit of circular cross-section is in its most stable position when lying on its side and accordingly requires at least three studs so disposed around the circumference to ensure tilting, for instance three studs at 120° to each other, or a functional equivalent, for example a ridge around its circumference.

A conventional circular tablet is in its most stable position when resting on either of its end faces and a squat parallelipiped is in its most stable position when resting on one of its largest faces. Thus a circular tablet or squat parallelipiped requires two projections one on each of the flat faces or largest faces respectively.

Where the unit has two end faces and a number of side faces as previously described, preferably it has two projections in the form of studs and preferably one stud is located centrally on each of the end faces.

Any orally-administrable medicament can be formulated as a shaped dosage unit in accordance with this invention. However, medicaments for the treatment of diseases where manual dexterity is imparied can be particularly advantageously formulated in accordance with the invention. Thus preferably the active ingredient is an anti-inflammatory, analgesic, anti-arthritic or anti-rheumatic agent. For example it can be aloxiprin, aspirin, azapropazone dihydrate, benorylate, buprofen, delta-chimotrypsin, dextropropoxyphene napsylate, diclotenac sodium, febuten, fenclotenac, fenoproten, feprazone, flurbiproten, flutenamic acid, hydroxychloroquine sulphate, indomethacin, ketoproten, metenamic acid, naproxen, oxyphenbutazone, paracetamol, penicillamine, phenylbutazone, piroxicam, sodium aurothiamalate, tolmetin or auranofin. In particular it is auranofin.

The dosage units of this invention can either comprise a shaped envelope with a content whose shape is with a content of medicament or consists of a shaped cohesive medicinal composition without an envelope. An example of a unit when it has a shaped envelope is a capsule. Examples which have no envelope are tablets and lozenges. Preferably the dosage unit is a shaped cohesive medicinal composition, in particular it is a tablet.

The dosage units of this invention can include pharmaceutical excipients. For example where the dosage unit is a tablet standard excipients include a filler, a compression aid, a lubricant, a binder, a disintegrant and a wetting agent. The fillers can be water-soluble or insoluble and examples are terra alba, sucrose and lactose. Typical compression aids are microcrystalline cellulose and dicalcium phosphate. Typical lubricants are stearic acid and its pharmaceutically acceptable alkali metal and amine salts. Examples of binders are polyvinyl-pyrrolidone, polyethylene glycol, natural gums (including veegum, tragacanth and acacia), starch paste and gelatin. Examples of disintegrants are alginates and their salts and maize and potato starches. Examples of wetting agents include sodium lauryl sulphate, polyoxyethylene surfactants and polysorbates.

Cohesive units can be film or sugar coated.

The dosage units of this invention can be prepared by forming the active ingredient with any excipient into the shape as previously defined.

The dosage unit can be formed into the shape by applying the shape to the exterior. For example the unit can be made by compressing the ingredients, that is, the active ingredient and any excipient, with a shaped punch and die. Alternatively the unit can be made by filling the ingredients into a shaped envelope, for example a shaped capsule shell.

Where the dosage unit of the invention is a tablet, it can be made by air milling or hammer-milling the active ingredient and where necessary the excipient, to a fine particle size mixing these ingredients and compressing with a punch and die.

Alternatively the milled ingredients can be granulated before or after mixing. An example of a dry granulation process comprises passing the milled ingredients through compression rollers to obtain a coarse compacted powder and passing the powder through a screen.

An example of a wet granulation process comprises wetting the mixed milled ingredients with water, ethanol, or a solution of a binding agent for example polyvinylpyrrolidone, passing the wetted mass through a coarse screen (No. 2 to 10 British Standard mesh size; 1.6 to 11 mm), drying the coarse granules and then passing the material through a fine screen. Granules can also be made using a fluid bed granulator, where the dry powder (that is dry milled ingredient) is added to the granulator, wetted by spraying and subsequently dried in situ.

Film or sugar coating can be applied to shaped cohesive medicinal compositions by standard techniques.

When the dosage unit has an envelope, the envelope providing the shape required can be made by moulding so that the projections are integral with the envelope or by affixing projections to a standard envelope. Thus a capsule shell with studs can be made by glueing a number of such studs to the exterior of the shell with an edible glue.

The invention will now be described by way of example with reference to the accompanying drawings where:

FIG. 1 is a perspective view of a dosage unit of the invention;

FIG. 1A is a plan view of the dosage unit of FIG. 1 from below;

FIG. 1B is a elevation of the dosage unit of FIG. 1 in a tilted position;

FIG. 2 is a perspective view of a further dosage unit of the invention;

FIG. 2A is a plan view of the further dosage unit of FIG. 3 from below;

FIG. 2B is a side elevation of the dosage unit of FIG. 5 in a tilted position;

FIG. 11 is a perspective view of a further embodiment of a dosage unit of this invention;

FIG. 11A is a plan view of the dosage unit of FIG. 11 from below;

FIG. 11B is a side elevation of the dosage unit of FIG. 11 in a tilted position;

FIG. 12 is a perspective view of the dosage unit of this invention;

FIG. 12A is a side elevation of the dosage unit of FIG. 12 in a tilted position;

FIG. 21 is a perspective view of a further embodiment of a dosage unit of this invention;

FIG. 21A is a plan view of the dosage unit of FIG. 21 from below;

FIG. 21B is a side elevation of the dosage unit of FIG. 21 in a tilted position;

FIG. 22 is a perspective view of a further embodiment of a dosage unit of this invention;

FIG. 22A is a plan view of the dosage unit of FIG. 22 from below;

FIG. 22B is a side elevation of the dosage unit of FIG. 22 in a tilted position;

FIG. 25 is a side elevation of a further embodiment of a dosage unit of this invention;

FIG. 25A is a end elevation of the dosage unit of FIG. 25 in a tilted position;

FIG. 28 is a side elevation of a further embodiment of a dosage of the invention in a tilted position;

FIG. 28A is a perspective view of the dosage unit of FIG. 28.

Figure 3:
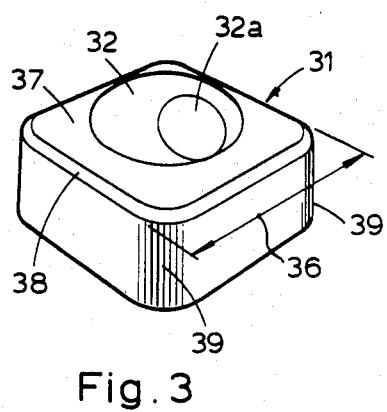
FIG. 3 is a perspective view of a further embodiment of a dosage unit of the invention.

With reference to FIGS. 1 to 1B, the unit has a main body indicated generally by 11 and fulcra provided by projections 12 and 13.

The main body 11 is in the shape of a squat regular trigonal prism, having a shortest main body dimensions 14, a longest main body dimension 15 and a lateral main body dimension 16.

The projections 12 and 13 are dome-shaped studs. One stud is positioned centrally on each of the triangular faces 17. The peripheral edges 18 of the large faces are chamfered. The corners 19 joining the triangular faces are rounded.

When resting on a flat surface, on a small face, that is a side face as shown in FIG. 1 the unit is in a metastable position and can be pushed over into the stable tilted position as shown in FIG. 1B where one stud 13 is in contact with the surface.

Referring to FIGS. 2 to 2B, the unit has a main body 21 and fulcra provided by projections 22 and 23.

The main body is a squat regular right parallelipiped having a shortest main body dimension 24 and two equal longest main body dimensions 25 and 26. The ratio of the longest dimension to the shortest dimension is 2.5:1. For example the longest dimensions are each 7.5 mm and the shortest dimension is 3 mm.

In this embodiment the projections 22 and 23 are domed-shaped studs. One stud is positioned centrally on each of the two largest faces 27 of the parallelipiped. The ratio of the small dimension to the radius of the domes is 1:1. The radius of the domes can be for example 3 mm.

The peripheral edges 28 of the largest faces 27 are chamfered. The angle of the chamfer is 45° and its vertical height is 0.25 mm. The corners 29 joining the largest faces 28 are rounded and their radius can be for example 1.5 mm.

When tipped from a container on to a flat surface the dosage unit can fall on to one of its smaller faces that is to say one of the side faces as shown in FIG. 2 or with one of the largest faces 27 downward. If the dosage unit is resting on the surface on a side face, it is in a metastable position and can be pushed over to a tilted position as shown in FIG. 2B, where the projection is in contact with the surface and the dosage unit is tilted. In this tilted position the centre of gravity of the dosage unit is at its lowest point above the surface and the dosage unit is in its most stable position.

The dosage units of FIGS. 3 to 6B are modifications of the unit of FIGS. 2 and 2B.

Figure 3A:
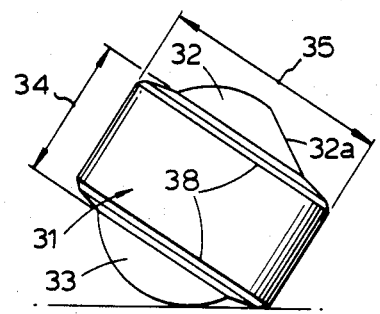
FIG. 3A is a side elevation of the dosage unit of FIG. 3 in a tilted position.

Referring to FIGS. 3 and 3A, the unit has a main body 31 in the shape of a squat regular right parallelipiped and projections provided by two dome-shaped studs 32 and 33, one of which is monofaceted 32a.

The main body 31 has a shortest dimension 34 and two equal longest dimensions 35 and 36. One stud is positioned centrally on each of the largest faces 37. The peripheral edges 38 of the largest faces are chamfered. The corners 39 joining the largest faces are rounded.

Figure 4:
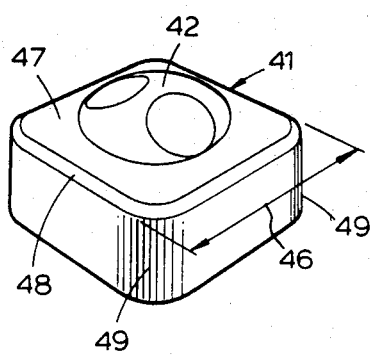
FIG. 4 is a perspective view of a further embodiment of a dosage unit of the invention.
Figure 4A:
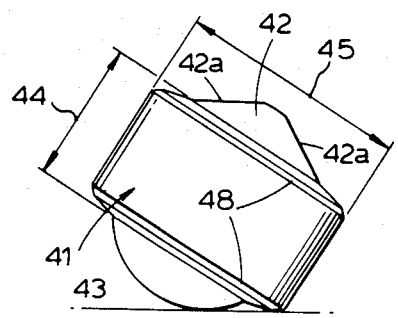
FIG. 4A is a side elevation of the dosage unit of FIG. 10 in a tilted position.

Referring to FIGS. 4 and 4A, the unit has a main body 41 in the shape of a squat regular right parallelipiped and projections provided by two dome-shaped studs 42 and 43, one of which is bifaceted 42a.

The main body 41 has a shortest dimension 44 and two equal longest dimensions 45 and 46. One stud is positioned centrally on each of the largest faces 47. The peripheral edges 48 of the largest faces are chamfered. The corners 49 joining the largest faces are rounded.

Figure 5:
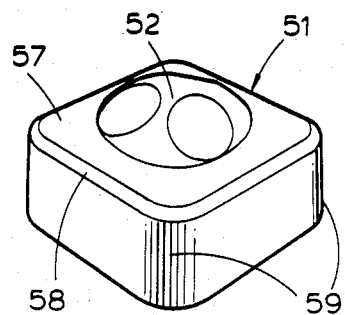
FIG. 5 is a perspective view of a further embodiment of a dosage unit of the invention.
Figure 5A:
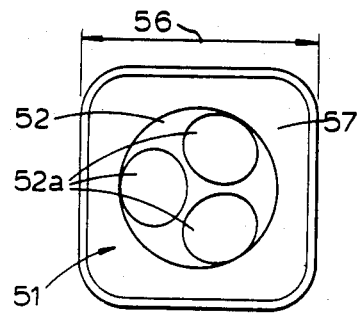
FIG. 5A is a side elevation of the dosage unit of FIG. 5 in a tilted position.
Figure 5B:
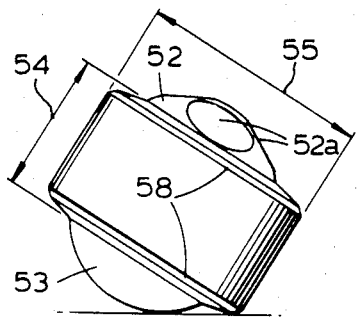

Referring to FIGS. 5 and 5A, the unit has a main body 51 in the shape of a squat regular right parallelipiped and projections provided by two dome-shaped studs 52 and 53, one of which is trifaceted 52a.

The main body 51 has a shortest dimension 54 and two equal longest dimensions 55 and 56. One stud is positioned centrally on each of the largest faces 57. The peripheral edges 58 of the largest faces are chamfered. The corners 59 joining the largest faces are rounded.

Figure 6B:
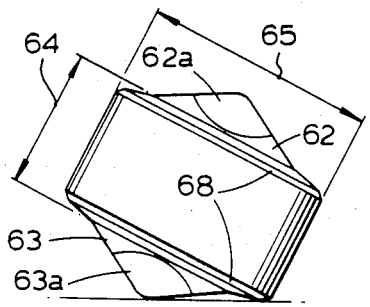
FIG. 6 is a perspective view of a further embodiment of a dosage unit of this invention.
FIG. 6A is a side elevation of the unit of FIG. 6 in a tilted position.
Figure 6:
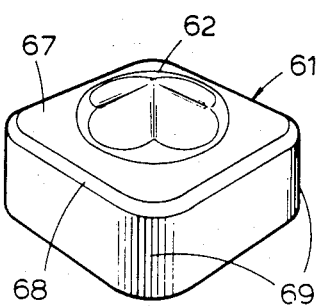
Figure 6A:
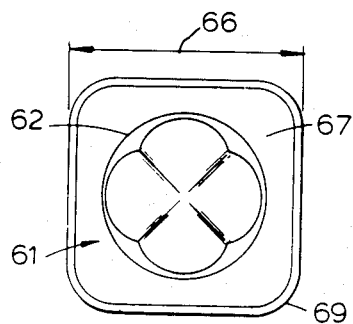

Referring to FIGS. 6 to 6B, the unit has a main body 61 in the shape of a squat regular parallelipiped and projections provided by two tetrafaceted dome-shaped studs 62 and 63.

The main body 61 has a shortest dimension 64 and two equal longest dimensions 65 and 66. One stud is positioned centrally on each of the largest faces 67. The peripheral edges 68 of the largest faces are chamfered. The corners 69 joining the largest faces are rounded.

Figure 7:
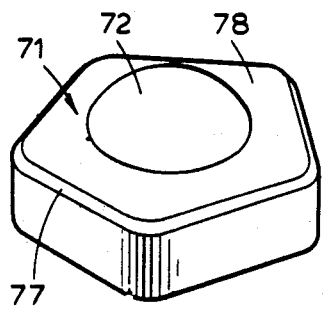
FIG. 7 is a perspective view of a further embodiment of a dosage unit of the invention.
Figure 7B:
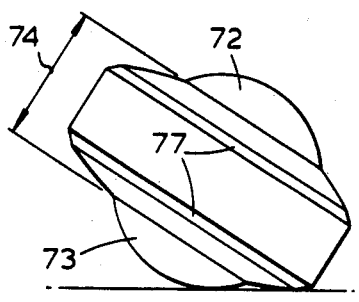
FIG. 7B is side elevation of the dosage unit of FIG. 7 in a tilted position.
Figure 7A:
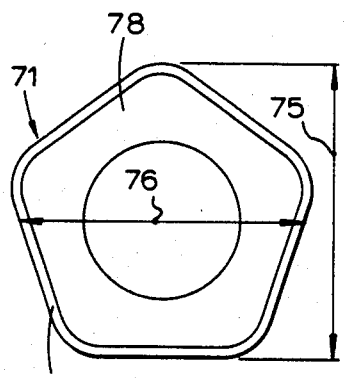
FIG. 7A is a plan view from below of the unit of FIG. 7.

With reference to FIGS. 7 to 7B, the main body 71 of the dosage unit is a squat regular pentagonal prism having a shortest main body dimensions 74, a longest main body dimension 75 and a lateral main body dimension 76.

The projections 72 and 73 are domed shaped studs, one of which is central on each of the pentagonal faces 78. The peripheral edges 77 of the pentagonal faces are chamfered. The corners joining the pentagonal faces are rounded.

When tipped from a container on to a flat surface the unit can fall on to one of its small faces, i.e. a side face as shown in FIG. 7 or with one of its largest faces 78 downward as shown in FIG. 7B. When resting on a side face the dosage unit is in a metastable position and can be pushed over into the stable tilted position as shown in FIG. 7B where one projection is in contact with the surface.

Figure 8A:
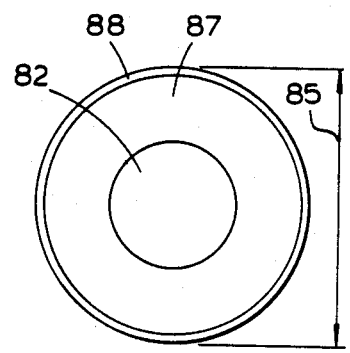
FIG. 8A is a plan view of the unit of FIG. 8 from below.
Figure 8:
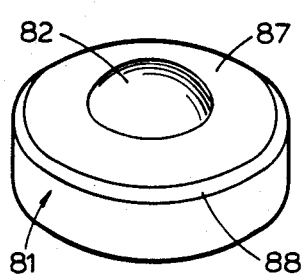
FIG. 8 is a perspective view of further embodiment of a dosage unit of the invention.
Figure 8B:
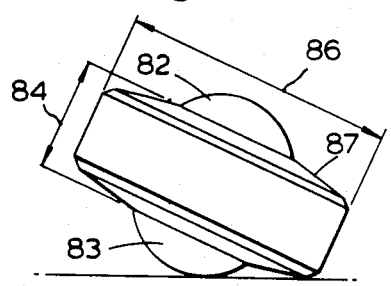
FIG. 8B is a side elevation of the dosage unit of FIG. 8 in a tilted position.

Referring to FIGS. 8 to 8B, the main body 81, of the unit is in the shape of a circular tablet having a shortest main body dimension 84 and two equal longest main body dimension 85 and 86. By way of example the shortest dimension 84 can be 4.8 mm, the longest dimensions 85 and 86 can be 11.6 mm and the height of the dome can be 1.7 mm.

In this embodiment the projections 82 and 83 are dome-shaped studs. One stud is positioned centrally on each of the circular, generally curved, convex faces 87.

The peripheral edges 88 of the largest faces 87 are chamfered.

When tipped from a container on to a flat surface, the dosage unit can fall on its curved face or with one of its large faces 87 downward as shown in FIG. 8B. If the unit is resting on its curved face, it is in a metastable position and can be pushed over to a position as shown in FIG. 8B where it is tilted.

Figure 9:
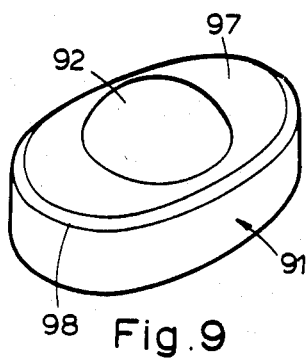
FIG. 9 is a perspective view of a further embodiment of a dosage unit of the invention.
Figure 9B:
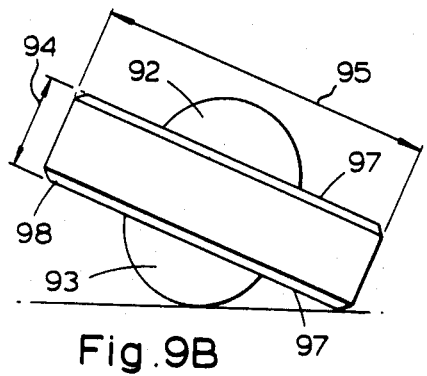
FIG. 9B is a side elevation of the dosage unit of FIG. 9 in a tilted position.
Figure 9A:
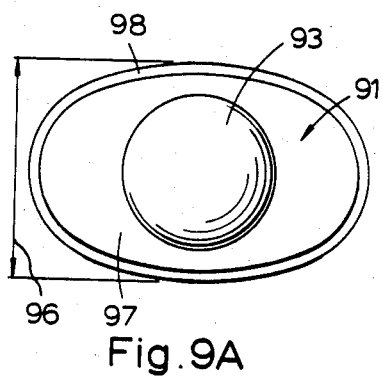
FIG. 9A is a plan view of the dosage unit of FIG. 9 from below.

With reference to FIGS. 9 to 9B, the main body 91 of the unit is an oblate cylinder, having a shortest main body dimension 94, a longest main body dimension 95, and a lateral main body dimension 96.

In this embodiment the projections 92 and 93 are dome-shaped, and one is located centrally on each of the elliptical faces 97. The edge 98 of each elliptical face 97 is chamfered.

Figure 10A:
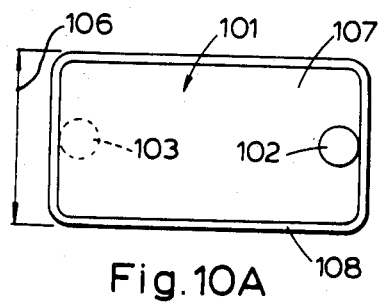
FIG. 10A is a plan view of the dosage unit of FIG. 10 from above.
Figure 10:
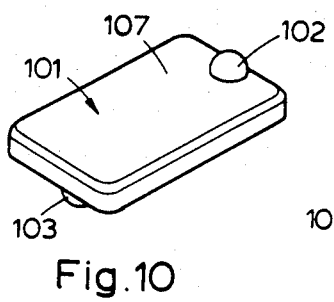
FIG. 10 is a perspective view of a further embodiment of a dosage unit of this invention.
Figure 10B:
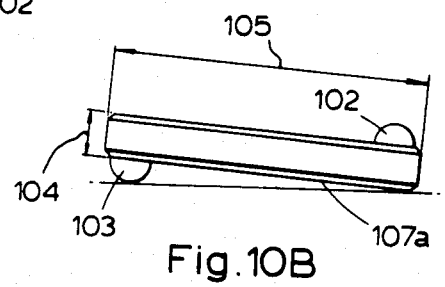
FIG. 10B is a side elevation of the dosage unit of FIG. 10 in a tilted position.

With reference to FIGS. 10 to 10B the main body 101 of the dosage unit is a squat parallelipiped having a shortest main body dimension 104, a longest main body dimension 105 and a lateral main body dimension 106. In this embodiment the projections 102 and 103 are hemispherical studs. One stud 102 is positioned on one largest face 107 in the middle of the shorter edge. The other projection 103 is positioned on the other largest face 107a in middle of the remote shorter edge.

When the dosage unit is resting with one largest face 107a downwards, one projection 103 is in contact with the surface and the unit is tilted as shown in FIG. 10B.

With reference to FIGS. 11 to 11B, the main body 111 of the unit is a squat parallelipiped having hemispherical studs 112 and 113. The main body 101 has a shortest dimension 114, a largest dimension 115 and a lateral dimension 116.

One stud 112 is located in one corner of one largest faces 117 and the other stud 113 is located in the diagonally opposite corner of the other largest face 117a. The edges 118 of the largest faces are chamfered and the corners 119 are rounded.

With reference to FIGS. 12 and 12A, the main body 121 in an elongate parellelipiped having two equal shortest main body dimensions 124 and 125 and one longest main body dimension 126. In this embodiment the projections 122 and 123 are hemispherical studs. One projection is positioned on each of the largest faces 128 towards one shortest edge and each is equi-distant from the centre of the main body.

Figure 13:
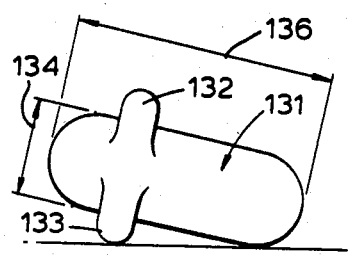
FIG. 13 is a side elevation of a further dosage unit of this invention in a tilted position.
Figure 13A:
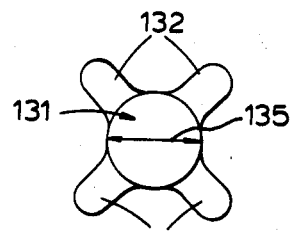
FIG. 13A is an end view of the embodiment of FIG. 13.

With reference to FIGS. 13 and 13A, the main body 131 of the dosage unit is capsule-shaped, that is cylindrical with domed ends. The unit has two equal short main body dimension 134 and 135 and a longest main dimension 136.

In this embodiment there are four radial projections 132 and 133 symmetrically disposed about a circumference of the unit towards one end. Each projection extends from the unit in a short cylindrical body portion and terminates in a domed end.

As can be seen in FIG. 13, when resting on a flat surface with two projections, the unit is supported in the tilted position by the projections.

Figure 14:
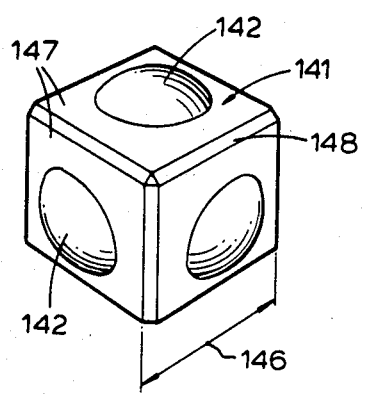
FIG. 14 is a perspective view of a further embodiment of a dosage unit of this invention.
Figure 14A:
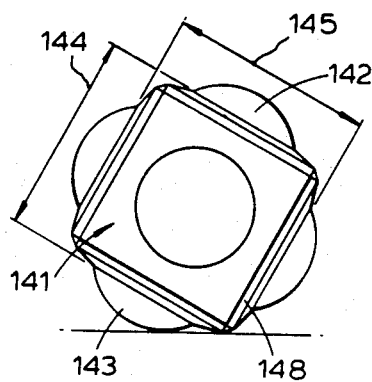
FIG. 14A is a side elevation of the dosage unit of FIG. 14 in a tilted position.

With reference to FIGS. 14 and 14A, the unit has a cubic main body 141 and projections provided by dome-shaped studs 142 and 143.

All the dimensions 144, 145 and 146 of the main body are equal.

One domed-shaped stud 142, 143 is located in the centre of each of the generally square-sided curved convex faces 147. The edges 148 of these generally square-sided faces are chamfered.

As shown in FIG. 14A, when the unit is resting in its most stable position on a horizontal flat surface one stud 143 is in contact with the surface and the unit is tilted relative to the horizontal by that stud.

Figures 15, 15B:
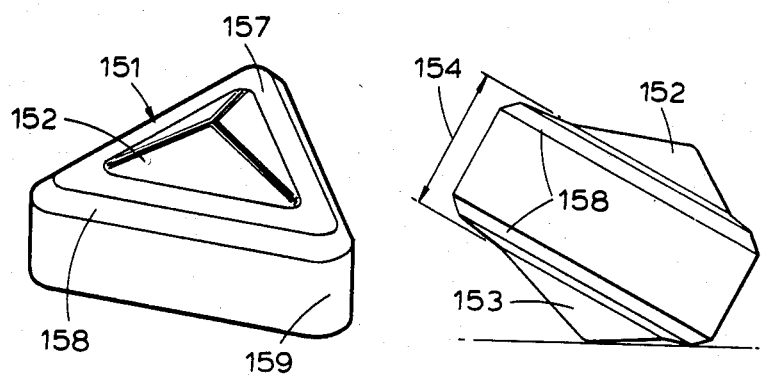
FIG. 15 is a perspective view of a further embodiment of a dosage unit of this invention.
FIG. 15B is a side elevation of the dosage unit of FIG. 15 in a tilted position.
Figure 15A:
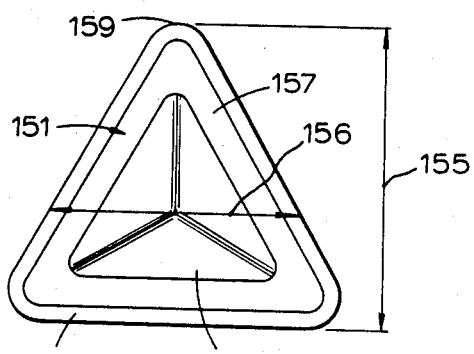
FIG. 15A is a plan view of the dosage unit of FIG. 15 from below.

With reference to FIGS. 15 to 15B, the dosage unit has a main body 151 in the shape of a trigonal prism. Projections are provided by trigonal pyramidal studs 152 and 153.

The main body has a shortest dimension 154, a longest dimension 155 and a lateral dimension 156. The studs 152 and 153 are located centrally one on each of the triangular end faces 157 of the main body. The edges 158 of the triangular faces 157 are chamfered. The corners 159 and the triangular faces 157 are rounded.

When it is in its most stable position on a horizontal flat surface the unit is tilted by one projection, for example 153, as shown in FIG. 15B.

Figure 16:
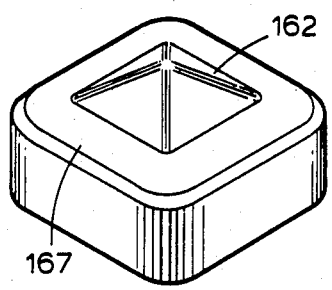
FIG. 16 is a perspective view of a further embodiment of a dosage unit of this invention.
Figure 16B:
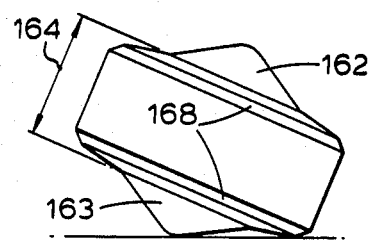
FIG. 16B is a side elevation of the dosage unit of FIG. 16 in a tilted position.
Figure 16A:
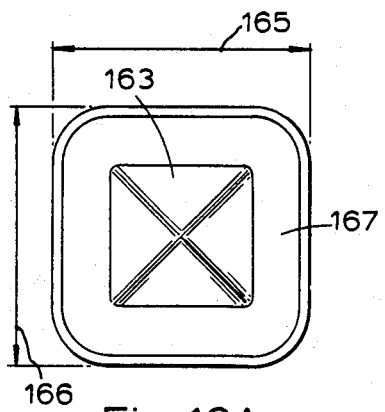
FIG. 16A is a plan view of the dosage unit of FIG. 16 from below.

With reference to FIGS. 16 and 16B, the main body of the dosage unit is a squat right parallelipiped. It has a shortest main body dimension 164 and two equal longer main body dimensions 165 and 166. The projections are provided by square pyramidal studs 162 and 163 which are located in the centre of each of the largest faces 167. The apecies of the pyramids are rounded.

The peripheral edges 168 of the largest faces are chamfered and the edges 169 joining the largest faces are rounded.

When resting on a flat surface with a largest face downward, as shown in FIG. 16B, one projection 163 is in contact with the surface and the unit is tilted.

Figure 17A:
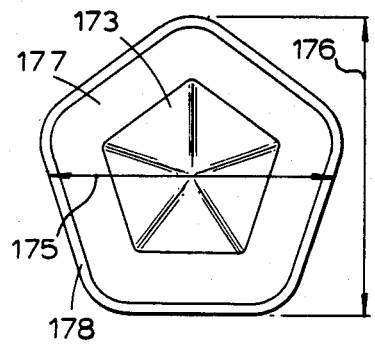
FIG. 17A is a plan view of the dosage unit of FIG. 17 from below.
Figure 17:
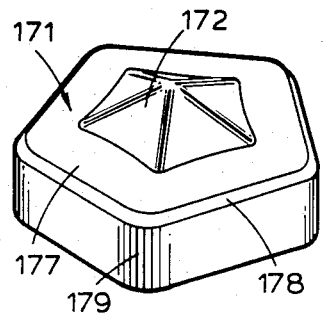
FIG. 17 is a perspective view of a further embodiment of a dosage unit of this invention.
Figure 17B:
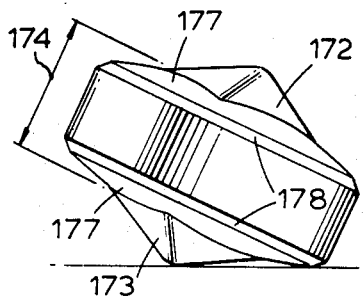
FIG. 17B is a side elevation of the dosage unit of FIG. 17 in a tilted position.

With reference to FIGS. 17 to 17B, the main body of the dosage unit is a regular pentagonal prism 17, having one shortest main body dimension 174, a longest main body dimension 175 and a lateral main body dimension 176. In this embodiment the projections are pentagonal pyramidal studs 172 and 173 one of which is positioned centrally on each of the largest faces 177. The faces of the pyramidal projections are fluted and the apecies are rounded.

The peripheral edges 178 of the largest faces 177 are chamfered and the edges 179 joining the largest faces are rounded.

When resting on a flat surface with a largest face downward as shown in FIG. 17B, one projection is in contact with the surface and the unit is tilted.

Figure 18:
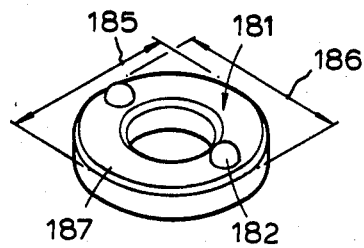
FIG. 18 is a perspective view of a further embodiment of a dosage unit of this invention.
Figure 18A:
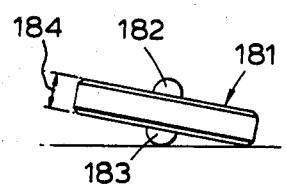
FIG. 18A is a side elevation of the dosage unit of FIG. 18 in a tilted position.

With reference to FIGS. 18 and 18A, the unit has a ring shaped main body 181 and projections provided by two pairs of hemispherical studs 182 and 183.

The main body has a shortest dimension 184 and the vertical axis lies through the centre of the ring. The other two dimensions 185 and 186 are equal.

The first pair of studs 182 is located one towards each end of a diameter on one flat end face 187 and the second pair of studs 183 is located on the other end face of the unit directly opposite the first pair.

As shown in FIG. 18A when the unit is resting in its most stable position on a horizontal flat surface with one pair of studs in contact with the surface, it is supported in a tilted position by the studs.

Figure 19:
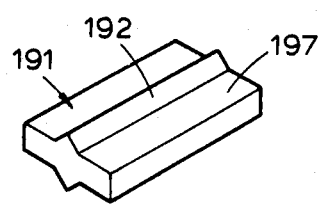
FIG. 19 is a perspective view of a further embodiment of a dosage unit of this invention.
Figure 19B:
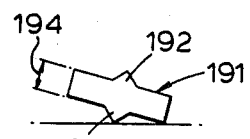
FIG. 19B is a end elevation of the dosage unit of FIG. 19 in a tilted position.
Figure 19A:
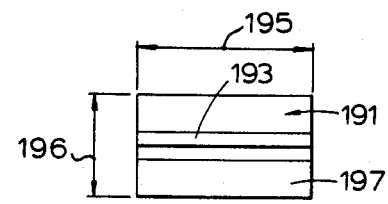
FIG. 19A is a plan view of the dosage unit of FIG. 19 from below.

With reference to FIGS. 19 to 19B, the unit has a squat parallelipipedal main body 191, a shortest main body dimension 194, a longest main body dimension 195 and a lateral main body dimension 196.

The projections are provided by ridges 192 and 193, one of each of which extends lengthway across the middle of each of the largest faces 197, parallel to the longest main body dimension. Each ridge has a triangular cross-section.

When the unit is resting with one of its largest faces 197 pointing downward, one ridge is in contact with the surface and the unit rests in a tilted position.

Figure 20:
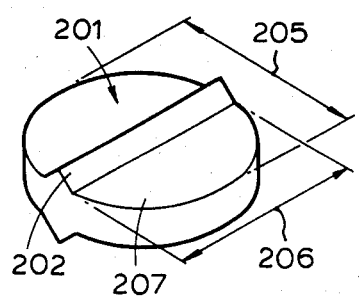
FIG. 20 is a perspective view of a further embodiment of a dosage unit of this invention.
Figure 20A:
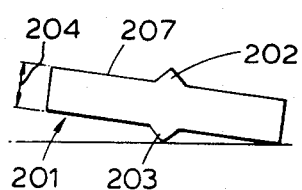
FIG. 20A is a side elevation of the dosage unit of FIG. 20 in a tilted position.

With reference to FIGS. 20 and 20A, the unit has projections provided by ridges 202 and 203. The main body 201 of the unit is a conventional circular tablet, that is, a squat right cylinder and has a shortest main body dimension 204 and two equal longest main body dimensions 205 and 206. The ridges, 202 and 203 which have a triangular cross-section, extend diametrically one across each flat face 207 of the tablet and are parallel to each other.

When in the tilted positioned as shown in FIG. 20A, one ridge 203 is in contact with the surface.

With reference to FIGS. 21 to 21B, the main body 211 of the unit is in the shape of an oblate paralellipiped. It has a shortest main body dimension 214, a longest main body dimension 215 and a lateral main body dimension 216. Projections are provided by regular tetragonal pyramidal studs 212 and 213, one of which is located centrally on each of the tetragonal end faces 217.

The tetragonal end faces 217 have chamfered peripheral edges 218 and rounded corners 219.

When resting on a flat surface with one tetragonal face downward, the unit is supported by one projection.

With reference to FIGS. 22 and 22A, the main body 221 of the dosage unit is an oblate cylinder having flat elliptical end faces 227. It has a shortest main body dimension 224, a longest main body dimension 225 and a lateral main body dimension 226. The projections are provided by ridges 222 and 223 which extend across the middle of each of the elliptical end faces 227 parallel to the lateral main body dimension 226. The ridges 222 and 223 are arched from end to end and have a triangular vertical cross-section with a rounded apex and an elliptical base.

The perpheral edges 228 of the largest faces 227 are chamfered.

When resting on a flat surface with one elliptical face down, the unit is supported in a tilted position by one of the ridges 223 as shown in FIG. 22A.

Figure 23:
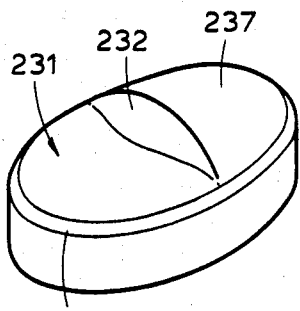
FIG. 23 is a perspective view of a further embodiment of a dosage unit of this invention.
Figure 23B:
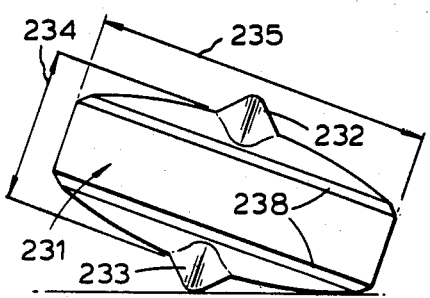
FIG. 23B is a side elevation of the dosage unit of FIG. 23 in a tilted position.
Figure 23A:
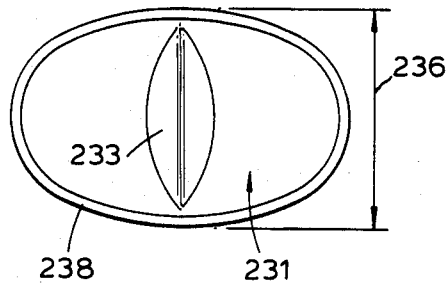
FIG. 23A is a plan view of the dosage unit of FIG. 23 from below.

With reference to FIGS. 23 to 23B, the main body 231 of the dosage unit is an oblate cylinder. It has a shortest main body dimension 234, a longest main body dimension 235 and a lateral main body dimension 236.

Projections are provided by ridges 232 and 233 which extend across the centre of each of the curved convex elliptical end faces 237 of the main body and are parallel to the lateral dimension 236.

The edges 238 of the elliptical faces 237 are chamfered. When the unit rests on a flat surface with one of its elliptical faces downward, a projection 233 is in contact with the surface and the unit is tilted.

Figure 24:
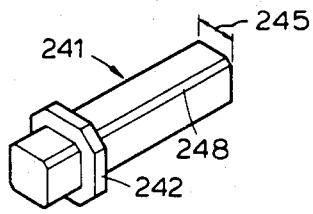
FIG. 24 is a perspective view of a further embodiment of a dosage unit of this invention.
Figure 24A:
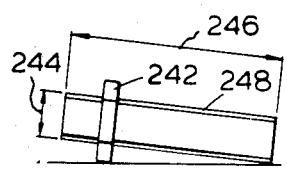
FIG. 24A is a side elevation of the dosage unit of FIG. 24 in a tilted position.

With reference to FIGS. 24 and 24A, the unit has an elongate parallelipipedal main body 241 and a projection provided by a peripheral ridge 242.

The main body 241 has two equal shortest main body dimension 244 and 245 and a longest main body dimension 246. The projection is provided by a ridge 242 which encircles the unit towards one end of the longest dimension 245.

The longest edges 248 of each of the largest faces 247 are chamfered, and the ridge 242 has chamfered portions 242a parallel to each of the champhered edges 248 of the largest faces.

When the unit is at rest, with the ridge 242 in contact with the flat surface, it is tilted as shown in FIG. 24A.

With reference to FIGS. 25 and 25A, the dosage unit, which in this embodiment is a capsule, has a main body 251 which is generally cylindrical with domed ends. A projection is provided by a circumferential ring shaped ridge 252 of circular cross-section.

The main body 251 has two equal shortest main body dimensions 254 and 255 and a longest main body dimension 256. The ring 252 encircles circumference of the main body towards one end of the longest dimension.

When resting with the projection in contact with the horizonal flat surface, the unit is tilted as shown in FIG. 25.

Figure 26:
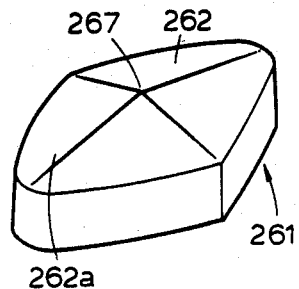
FIG. 26 is a perspective view of a further embodiment of a dosage unit of this invention.
Figure 26B:
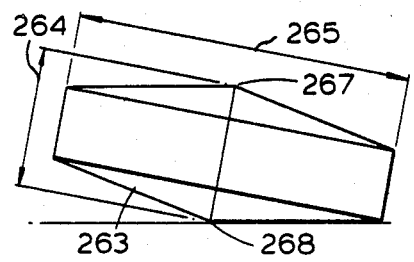
FIG. 26B is a side elevation of the dosage unit of FIG. 26 in a tilted position.
Figure 26A:
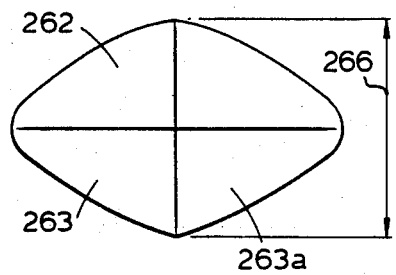
FIG. 26A is a plan view of the dosage unit of FIG. 26 from below.

With reference to FIGS. 26 and 26B, the unit is a composite shape made up of a substantially oblate cylinder 261 having tetragonal pyramidal end faces 262 and 263. The unit has a shortest dimension 264, a longest dimension 265 and a lateral dimension 266. Fulcra 267 and 268 are provided on the wholly convex surface by points formed by the intersection of four planar facets 262a and 263a on each pyramidal end face 262 and 263 respectively.

When on a flat surface with one pyramidal face 263 downward, the unit rests in a tilted position on one facet 263a as shown in FIG. 26B.

Figure 27A:
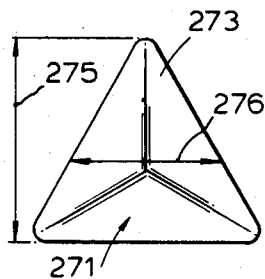
FIG. 27A is a plan view of the dosage unit of FIG. 27 from below.
Figure 27:
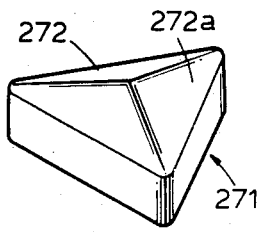
FIG. 27 is a perspective view of a further embodiment of a dosage unit of this invention.
Figure 27B:
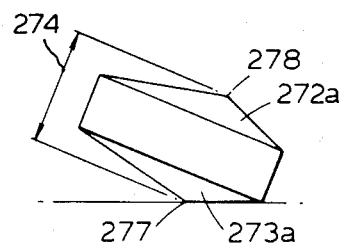
FIG. 27B is a side elevation of the dosage unit of FIG. 27 in a tilted position.

With reference to FIGS. 27 to 27B, the unit is a composite shape made up of a squat regular trigonal prism 271 having trigonal pyramidal end faces 272 and 273 and has a wholly convex surface. The unit has a shortest dimension 274, a longest dimension 275 and a lateral dimension 276. Fulcra 277 and 278 are provided by points formed by the intersection of three planar facets 272a and 273a on each of the pyramidal end faces 272 and 273 respectively.

With reference to FIGS. 28 and 28A, the unit is rectangular bipyramid. It has a shortest dimension 281 a longest dimension 282 and a lateral dimension 283. Fulcra 284 and 285 are provided by the intersection of contiguous planar faces for example 286 and 287.

As shown in FIG. 28, when resting in its most stable position on a horizontal flat surface, the unit is tilted.

The units of FIGS. 29 to 31A are a modification of the unit of FIGS. 8 to 8B.

Figure 29:
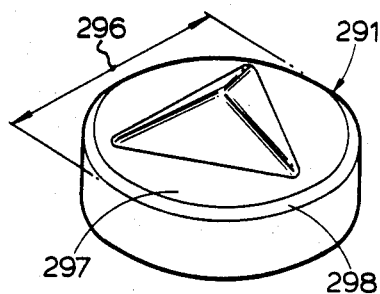
FIG. 29 is a perspective view of a further embodiment of a dosage unit of this invention.
Figure 29A:
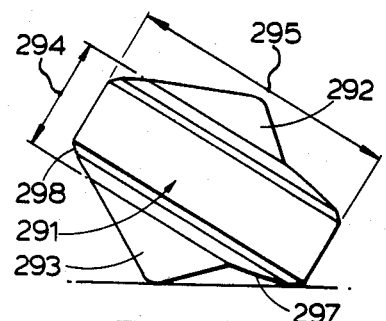
FIG. 29A is a side elevation of the dosage unit of FIG. 16 in a tilted position.

Referring to FIGS. 29 to 29A, the main body 291, of the unit is in the shape of a circular tablet having a shortest main body dimension 294 and two equal longest main body dimension 295 and 296.

In this embodiment the projections 292 and 293 are trigonal-pyramidal studs. One stud is positioned centrally on each of the circular, generally curved, convex faces 297.

The peripheral edges 298 of the largest faces 297 are chamfered.

When tipped from a container on to a flat surface, the dosage unit can fall on its curved face or with one of its large faces 297 downward as shown in FIG. 29A. If the unit is resting on its curved face, it is in a metastable position and can be pushed over to a position as shown in FIG. 29A where it is tilted.

Figure 30:
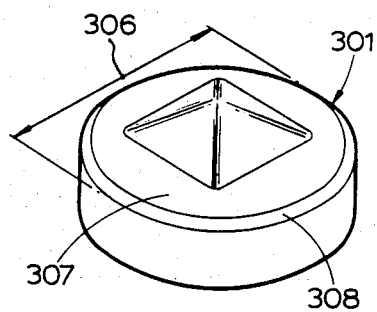
FIG. 30 is a perspective view of a further embodiment of a dosage unit of this invention.
Figure 30A:
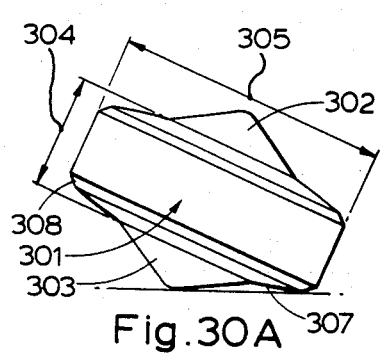
FIG. 30A is a side elevation of the dosage unit of FIG. 30 in a tilted position.

Referring to FIGS. 30 and 30A, the main body 301, of the unit is in the shape of a circular tablet having a shortest main body dimension 304 and two equal longest main body dimension 305 and 306. By way of example the shortest dimension 304 can be 4.8 mm, the longest dimensions 305 and 306 can be 11.6 mm and the height of the dome can be 1.7 mm.

In this embodiment the projections 302 and 303 are square-pyramidal studs. One stud is positioned centrally on each of the circular, generally curved, convex faces 307.

The peripheral edges 308 of the largest faces 307 are chamfered.

When the unit is resting with a large face 307 downward, as shown in FIG. 30A, it is tilted by the projection 303.

Figure 31:
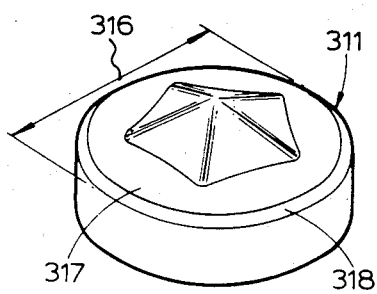
FIG. 31 is a perspective view of a further embodiment of a dosage unit of this invention and FIG. 31A is a side elevation of the dosage unit of FIG. 31 in a tilted position.
Figure 31A:
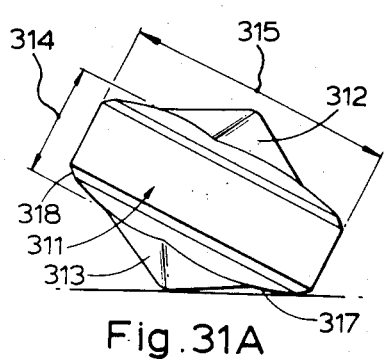

Referring to FIGS. 31 and 31A, the main body 311, of the unit is in the shape of a circular tablet having a shortest main body dimension 314 and two equal longest main body dimension 315 and 316.

In this embodiment and projections 312 and 313 are pentagonal-pyramidal studs. One stud is positioned centrally on each of the circular, generally curved, convex faces 317.

The peripheral edges 318 of the largest faces 317 are chamfered.

When the unit is resting on a flat surface with one of its large faces 317 downward as shown in FIG. 31A, it is tilted by the projection 313.

The following Examples illustrate the invention.

EXAMPLES

EXAMPLE 1

A tablet was made up from the following ingredients:

|  | mg per tablet |
|---|---|
| Auranofin | 6.0 |
| Lactose | 231.0 |
| Maize Starch | 31.0 |
| Microcrystalline Cellulose | 31.0 |
| Sodium Starch Glycollate | 15.5 |
| Magnesium Stearate | 1.55 |
| TOTAL | 316.05 |

Auranofin and maize starch were mixed together with sufficient lactose to produce a homogeneous mixture (the first mixture). The remaining lactose was mixed with the microcrystalline cellulose and sodium starch glycollate (the second mixture). The first and second mixtures were then mixed together and the magnesium stearate was mixed in. This final mixture was compressed on punches and dies so shaped as to form a tablet as shown in any one of the accompanying drawing Particularly FIGS. 1 to 11B, 14 to 17B and 21 to 23B.

A polymer aqueous film coating solution was prepared by adding hydroxypropylmethylcellulose—viscosity 5 cps (3.72 kg), hydroxymethylcellulose—viscosity 15 cps (3.72 kg) and propylene glycol (0.74 kg) to stirring purified water (80 kg). The mix was stirred for 30 min and left to stand to de-aerate (ca 16 hr). The mixture was then made up to 100 kg with purified water.

A quantity of tablets were loaded into a conventional rotating drum spray coating machine and lose dust was removed by tumbling the tablets through a hot air (90° C.) stream for a short period (ca 10 seconds). The tablets were then sprayed and dryed alternately with the polymer aqueous film coating solution using an electronically timed spray gun which intermittently sprays the tumbling tablets with the solution. The period of spraying and subsequent drying periods were set so that the tablets were not visibly wet at any time. The spraying/drying cycle was continued until the tablets were coated.

The coated tablets were transfered to a canvas polishing pan, mixed with finely powdered canuba wax (250 microns) and rolled until a sheen had developed.

EXAMPLE 2

| Ingredients | mg per Tablet |
|---|---|
| Auranofin | 6.0 |
| Lactose | 231.0 |
| Pregelatinized Starch N.F | 31.0 |
| Microcrystalline Cellulose | 31.0 |
| Sodium Starch Gycollate | 15.5 |
| Magnesium Stearate | 1.55 |

Auranofin, lactose and starch are granulated with water. The granulation is dried overnight and sized through a 840 microns screen. The granulation is then mixed with the remaining ingredients and compressed into tablets employing punches and dies so shaped as to form a tablet as shown in any one of the accompanying drawing particularly FIGS. 1 to 11B, 14 to 17B and 21 to 23B.

We claim:

1. An orally administrable pharmaceutical dosage unit comprising a solid main body having at least two main faces, each of said main faces having tilting means such that the most stable position of said dosage unit on a horizontal flat surface is a tilted position, said tilting means being free of any cutting edge formations.

2. A dosage unit according to claim 1, wherein said tilting means is centrally located on each of said main faces.

3. A dosage unit according to claim 1, wherein said tilting means is a projection on each of said main faces, any edges or points on said projection being chamfered or rounded.

4. A dosage unit according to claim 3, wherein said tilting means is centrally located on each of said main faces.

5. An orally administrable pharmaceutical dosage unit comprising a solid main body having at least two main faces, each of said main faces having tilting means centrally located thereon such that the most stable position of said dosage unit on a horizontal flat surface is a tilted position.

6. A dosage unit according to claim 5, wherein said main faces are elliptical and said tilting means are dome-shaped projections.

7. A dosage unit according to claim 6, wherein the active ingredient is an $H_2$ receptor antagonist.

8. A dosage unit according to Claim 5 wherein said main faces are in the shape of trigonal prism and said tilting means are dome-shaped projections.

9. A dosage unit according to Claim 5 wherein said main faces are in the shape of a circular tablet and said tilting means are dome-shaped projections.

10. A dosage unit according to Claim 5 wherein said main faces are in the shape of a circular tablet and said tilting means are pentagonal-pyramidal shaped projections.

* * * * *